United States Patent
Sogaro

(10) Patent No.: US 8,197,448 B2
(45) Date of Patent: Jun. 12, 2012

(54) DEVICE FOR RETAINING AND DISPENSING A FREE-FLOWING SUBSTANCE

(75) Inventor: Alberto C. Sogaro, Kronberg (DE)

(73) Assignee: Sulzer Mixpac AG, Haag (CH)

( * ) Notice: Subject to any disclaimer, the term of this patent is extended or adjusted under 35 U.S.C. 154(b) by 0 days.

(21) Appl. No.: 13/044,232

(22) Filed: Mar. 9, 2011

(65) Prior Publication Data

US 2011/0155763 A1   Jun. 30, 2011

Related U.S. Application Data

(62) Division of application No. 11/625,587, filed on Jan. 22, 2007, now Pat. No. 7,927,312.

(30) Foreign Application Priority Data

Jan. 24, 2006   (EP) ..................................... 06001463

(51) Int. Cl.
*A61M 5/00*   (2006.01)

(52) U.S. Cl. ........ 604/187; 604/195; 604/243; 604/256; 604/257

(58) Field of Classification Search ............... 604/68–72, 604/82–92, 164.02, 164.04, 164.07, 186, 604/187, 195, 198, 231, 232, 240–241, 243, 604/256–257, 275; 222/206, 209, 213, 214, 222/215, 633, 631, 632; 401/183–186
See application file for complete search history.

(56) References Cited

U.S. PATENT DOCUMENTS

| 3,157,323 | A |   | 11/1964 | Kitterman |
|---|---|---|---|---|
| 3,674,181 | A |   | 7/1972 | Marks et al. |
| 3,921,864 | A | * | 11/1975 | Dawes ........................ 222/386 |
| 4,192,524 | A | * | 3/1980 | Twiestmeyer ............. 280/416.1 |
| 5,071,413 | A |   | 12/1991 | Utterberg |
| 5,135,507 | A |   | 8/1992 | Haber et al. |
| 5,494,196 | A |   | 2/1996 | Tyner |
| 5,817,066 | A | * | 10/1998 | Goforth ....................... 604/212 |

(Continued)

FOREIGN PATENT DOCUMENTS

EP   0112574 A1   7/1984

(Continued)

OTHER PUBLICATIONS

European Search Report, EP 1 797 920, Apr. 13, 2007.

*Primary Examiner* — Quynh-Nhu H Vu
(74) *Attorney, Agent, or Firm* — Quarles & Brady LLP

(57) ABSTRACT

A device for retaining and dispensing a free-flowing substance includes a syringe-like retaining body (12) in which a retaining space (46) is formed. A displaceable piston (22) is axially introduced into the retaining space (46) and the retaining body (12) is provided with a dispensing nozzle (18) on its front end facing away from the piston (22). A locking pin (36) through which at least one transverse channel (44) passes, with an axial channel (42) branching off therefrom, is provided on the inside of the dispensing nozzle (18). In a closed position of the locking pin (36), a flow connection between the retaining space (46) and the transverse channel (44) is blocked. In an activation position of the locking pin (36), the transverse channel (44) is connected to the retaining space (46), so that the free-flowing substance can be dispensed from the retaining space (46) via the transverse channel (44) and the axial channel (42).

12 Claims, 8 Drawing Sheets

U.S. PATENT DOCUMENTS

| | | |
|---|---|---|
| 6,106,502 A | 8/2000 | Richmond |
| 6,162,200 A * | 12/2000 | Sawa et al. .................... 604/230 |
| 6,227,736 B1 | 5/2001 | Sogaro |
| 6,405,905 B1 | 6/2002 | Sogaro |
| 6,447,476 B1 * | 9/2002 | Sogaro ........................... 604/85 |
| 6,547,101 B1 | 4/2003 | Sogaro |
| 6,613,021 B2 | 9/2003 | Sogaro |
| 6,719,729 B2 | 4/2004 | Sogaro |
| 6,723,074 B1 | 4/2004 | Halseth |
| 7,100,802 B2 | 9/2006 | Sogaro |
| 7,367,964 B2 * | 5/2008 | Heinz et al. ................... 604/263 |
| 7,861,897 B2 | 1/2011 | Sogaro |
| 7,927,312 B2 * | 4/2011 | Sogaro ........................... 604/187 |

FOREIGN PATENT DOCUMENTS

| | | |
|---|---|---|
| WO | WO9618552 A1 | 6/1996 |
| WO | WO0020057 A1 | 4/2000 |
| WO | WO03100424 A2 | 12/2003 |

* cited by examiner

DEVICE FOR RETAINING AND DISPENSING A FREE-FLOWING SUBSTANCE

CROSS REFERENCES TO RELATED APPLICATIONS

This application is a divisional of U.S. patent application Ser. No. 11/625,587 filed on Jan. 22, 2007 now U.S. Pat. No. 7,927,312, which claims the priority benefit of European Patent Application No. 06 001 463.6 filed on Jan. 24, 2006, both of which are fully incorporated herein by reference.

STATEMENT REGARDING FEDERALLY SPONSORED RESEARCH

Not Applicable.

DESCRIPTION OF THE BACKGROUND ART

The invention involves a device for retaining and dispensing a free-flowing substance having a syringe-like retaining body in which a retaining space is formed and a displaceable piston is axially introduced, whereby the retaining body is provided on its front end facing away from the piston with an essentially cylindrical dispensing nozzle. Such a device is known from practice and is used in the medical field, for example, in the form of a syringe for injecting medications. Such a syringe comprises a retaining body in which there is a retaining space for the free-flowing substance and in which a displaceable piston is axially introduced. On its front end facing away from the piston, the retaining body is equipped with an essentially cylindrical dispensing nozzle to which may be attached a cannula or some other application unit. Such syringes are usually designed as disposable syringes and are discarded after use.

SUMMARY OF THE INVENTION

The object of the invention is to provide a device of the generic design described above which is suitable for multiple applications, whereby the free-flowing substance can be stored in the retaining space of the retaining body in a protected manner between individual applications.

This objective is achieved by providing the device with a locking pin is provided on the inside of the dispensing nozzle. At least one transverse channel passing through the locking pin has an axial channel branching off from it. In a closed position of the locking pin, a flow connection between the transverse channel and the retaining space is blocked. In an activation position of the locking pin, a flow connection between the transverse channel and the retaining space is released, so that the free-flowing substance can be dispensed from the retaining space via the transverse channel and the axial channel.

The locking pin is introduced on the inside of the dispensing nozzle, which is penetrated by at least one transverse channel, from which an axial channel branches off. In a closed position of the locking pin, a flow connection between the transverse channel and the retaining space is blocked. In an activation position of the locking pin, a flow connection is released between the transverse channel and the retaining space, so that the free-flowing substance can be dispensed from the retaining space via the transverse channel and the axial channel.

Thus, a device for retaining and dispensing a free-flowing substance is provided, designed in the manner of a syringe. The locking pin is designed in the manner of a stopper which is inserted into the dispensing nozzle and whose position in the outlet connection either blocks or releases delivery of the free-flowing substance.

The retaining body and thus the dispensing nozzle integrally molded on the retaining body are preferably made of a chemically resistant plastic, so the device may also be used in combination with medications and/or test substances in particular that are used in the field of analysis.

To introduce an additional substance into the retaining space and be able to dissolve it in a test liquid there, a special embodiment of the device incorporating the invention has a lateral insertion channel for the substance on the retaining body. For example, a cotton swab loaded with a sample is introduced via the insertion channel into a test liquid already present in the retaining space so that the sample is dissolved in the test fluid. The fluid, which has been loaded with the sample, may then be dispensed from the device for analytical purposes by operating the piston after the locking pin has been brought into the active position. Even with the piston retracted, air can flow through the lateral insertion channel into a space situated above the test liquid, so that it can be dissolved at least proportionately in the test liquid upon depressing the piston. The insertion channel may be designed in particular as a one-sided funnel-like widening in a side wall of the retaining body in the end area facing away from the dispensing nozzle.

In a special embodiment of the device incorporating this invention, the dispensing nozzle has at least one ring-shaped sealing lip on its interior side on which the locking pin is fitted. A device designed in this way operates in such a way that the transverse channel is arranged on the side of the sealing lip facing away from the retaining space in the closed position of the locking pin, and in the activation position of the locking pin, it communicates with the retaining space. Two ring-shaped sealing lips are preferably provided on the inside of the dispensing nozzle, and the transverse channel preferably has a diameter that is equal to or less than the distance between the two sealing lips.

In an alternative embodiment of a device incorporating this invention, the locking pin engages with a seal in an outlet opening of the retaining space to block the flow connection between the retaining space and the transverse channel. To increase the sealing effect in the closed position with a device designed in this way, the locking pin preferably has a conical sealing surface which interacts with a corresponding surface on the dispensing nozzle, which is connected to the outlet opening.

The locking pin, which interacts with the sealing lips on the inside of the dispensing nozzle, may in particular be a component of an application device, such as a cannula, a pipetting tip or the like. However, the locking pin can also be a separate component without departing from the scope of the invention. A separate locking pin can be pressed onto the dispensing nozzle in the direction of the retaining space of the retaining body when an application device is attached. Pressing the locking pin onto the dispensing nozzle displaces the locking pin into the activation position, thereby establishing a flow path between the retaining space and the application device via the transverse channel and the axial channel of the locking pin.

The application device may also be provided with a nozzle through which, on operation of the piston, the substance contained in the retaining space can be dispensed, e.g., in atomized form, after moving the locking pin into the activation position.

To implement an automatically reclosable device, the locking pin may be spring biased in the closing direction. Thus, the locking pin is displaced into the activation position when an application device is attached to it, for example, but this is cancelled when the application unit is removed, in such a way that the locking pin automatically snaps back into the closed position. In order that the spring not come in contact with the free-flowing substance and possibly contaminate it, the spring is supported in encapsulated form in a special embodiment of the device incorporating the invention. For example, the spring surrounds the dispensing nozzle, the spring being supported on a support of the dispensing nozzle at one end and on the locking pin or an application device tightly connected to the locking pin at the other end.

To prevent the locking pin from being loosened from the dispensing nozzle on operation of the piston, the locking pin is preferably interconnected with the dispensing nozzle using a catch mechanism. In a special embodiment of the device incorporating the invention, an application device or an adapter device on which the locking pin originates, exhibits at least two legs which extend from a base plate in the direction of the retaining space essentially parallel to the axis of the axial channel, a catch nose being designed on each leg, interacting with a corresponding catch collar on the circumference of the dispensing nozzle. Such a catch mechanism ensures that the application device or the adapter device with the locking pin will not become detached from the dispensing nozzle when the free-flowing substance is dispensed from the retaining space.

Fixation devices which interact with corresponding components of the locking pin and can thus secure them in the closed position and/or in the activation position are preferably provided on the outside of the dispensing nozzle. Such fixation devices and catch mechanisms on the outside of the dispensing nozzle may also serve in particular as supports for the spring for positioning of the locking pin so it is biased in the closed position.

Additional advantages and advantageous embodiments of the subject of the invention can be derived from the description, the drawing and the patent claims.

BRIEF SUMMARY OF THE DRAWINGS

Three exemplary embodiments of a device for retaining and dispensing a free-flowing substance designed incorporating this invention are shown in simplified schematic diagrams in the drawings and explained in greater detail in the following description.

DETAILED DESCRIPTION OF THE PREFERRED EMBODIMENTS

Figure 1:
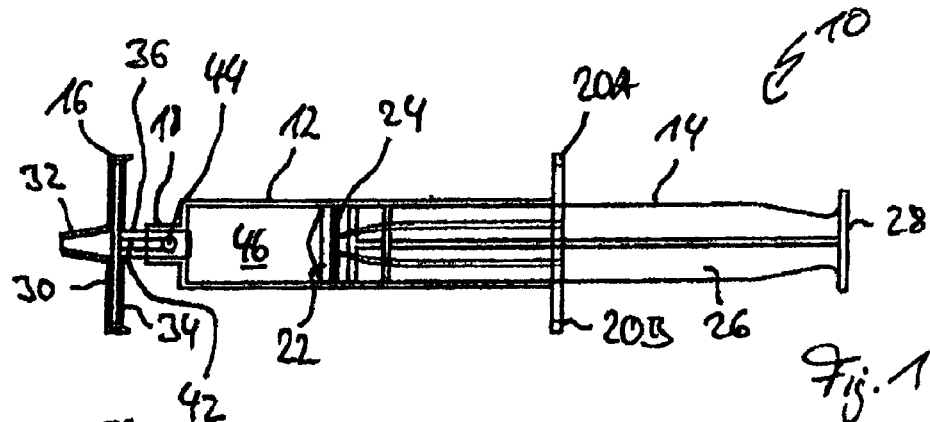
FIG. 1 is a side view of a syringe-like device in the closed position.

FIGS. 1 through 6 show a device 10 for storing and dispensing a free-flowing substance, e.g., a test liquid to which a saliva sample has been added. The device 10 is comprised of essentially three components, namely an essentially cylindrical retaining body 12, a piston unit 14 and an application device 16.

The retaining body 12 is comprised of an essentially cylindrical base body which is equipped with a dispensing nozzle 18 on the front end, likewise having a cylindrical design. On its end facing away from the dispensing nozzle 18 the retaining body 12 has two grip straps 20A and 20B where a ring finger and a middle finger of a user may grip the device during operation of the piston unit 14.

The piston unit 14 has a cylindrical piston 22 equipped with a sealing lip 24 on its circumference. The piston 22 is connected via a piston rod 26 to a pressure plate 28 where a finger, in particular the user's thumb, can rest.

The application unit 16 is designed as an application device which is formed from an front plate 30 with a nozzle 32 and a sealing plate 34 on which a locking pin 36 is integrally molded. A filter (not shown here) or the like may be arranged between the frontal face plate 30 and the sealing plate 34. The locking pin 36 is inserted into the dispensing nozzle 18 of the retaining body 12 and cooperates with two sealing lips 38 and 40 which are spaced a distance apart in the axial direction of the retaining body and which are designed in one piece on the inside of the dispensing nozzle 18.

The locking pin 36 has an axial channel 42 which opens on the side of the sealing plate 34 facing frontal plate 30 and is connected to a transverse channel 44 which passes through the locking pin 36. Transverse channel 44 has a diameter somewhat smaller than the axial distance between the two sealing lips 38 and 40 so that locking pin 36 is arranged in a closed position when transverse channel 44 is situated between the two sealing lips 38 and 40 and the locking pin is positioned in an activation position when transverse channel 44 is advanced beyond the sealing lips 40 into a retaining space 46 of the retaining body 12 so that a liquid contained in the retaining space 46 can be dispensed through transverse channel 44, axial channel 42 and nozzle 32 by depressing piston unit 14.

The retaining body 12 includes a distal cylindrical section 48 connected to an interrupted cylindrical section 50 which is provided with an insertion channel 52 that opens outward in a funnel shape. Use of the device 10 is explained in greater detail below with reference to FIGS. 1 through 4.

In a starting position, the locking pin 36 of application unit 16 is in a closed position in which transverse channel 44 is arranged between the two sealing lips 38 and 40. In addition retaining space 46 is filled with a test liquid and piston 22 is slidably inserted into retaining body 12 in the direction of the dispensing nozzle 18 a sufficient distance to seal the retaining space 46 in the direction of the insertion channel 52. Piston 22 is thus situated in the front cylindrical section 48 of the retaining body 12.

Figure 2:
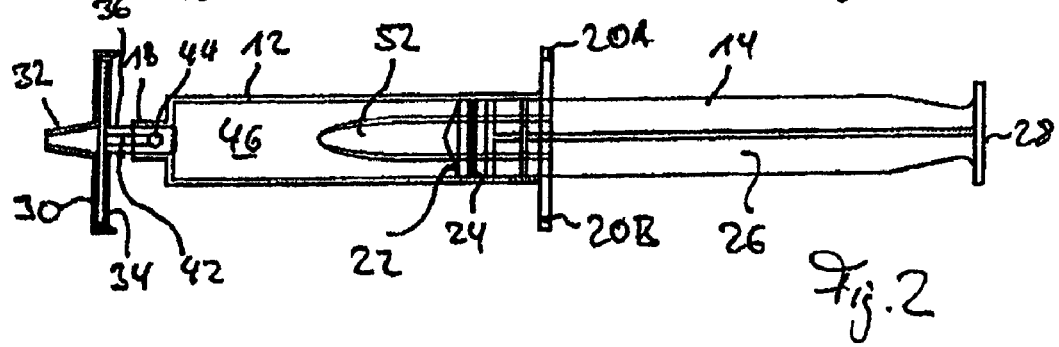
FIG. 2 shows the device according to FIG. 1 with the piston retracted.
Figure 3:
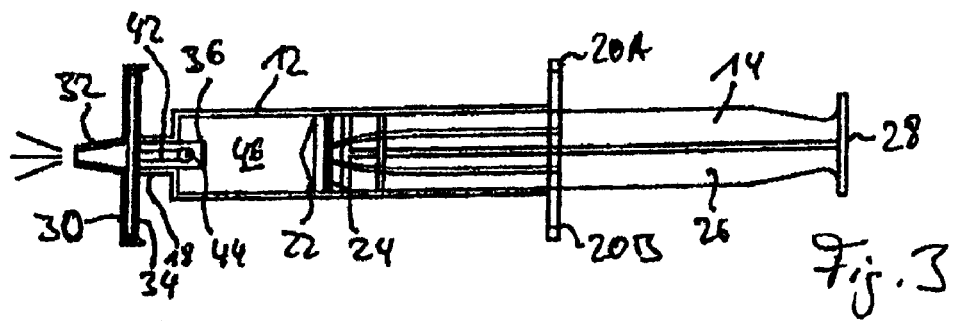
FIG. 3 shows the device according to FIG. 1 in the activation position.
Figure 4:
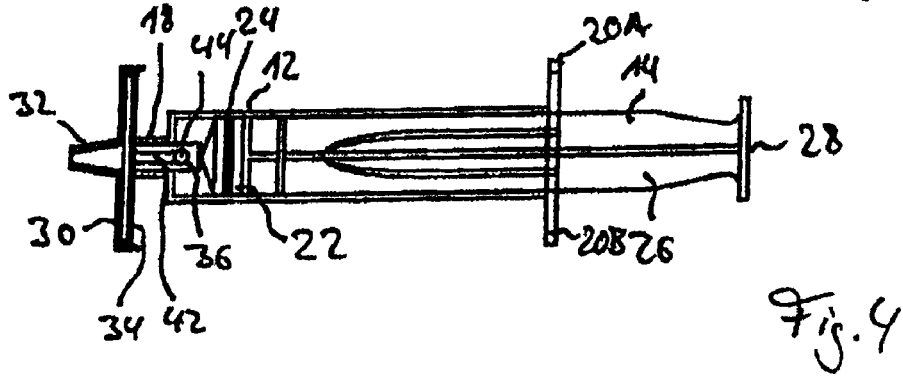
FIG. 4 shows the device according to FIG. 1 in the activation position after emptying.
Figure 5:
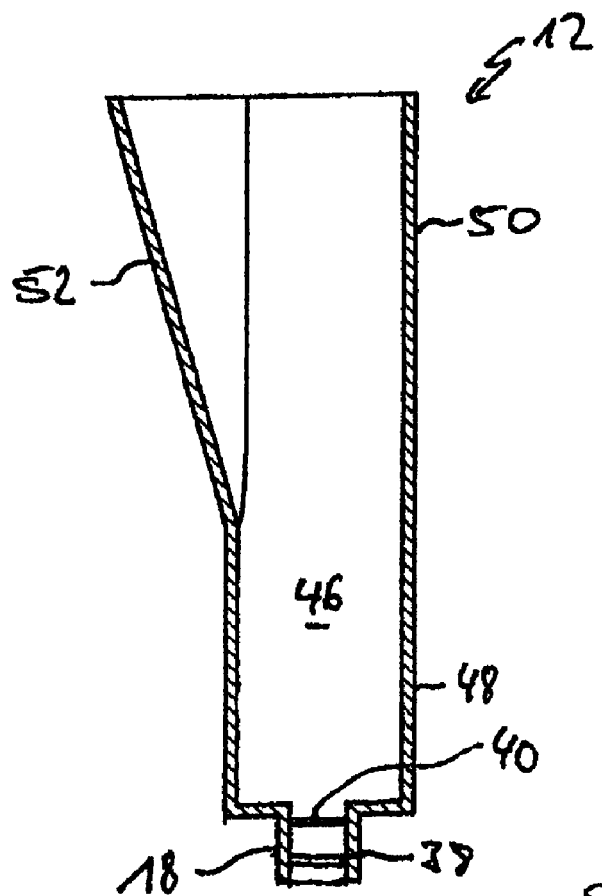
FIG. 5 is a longitudinal section view through a retaining body of the device according to FIG. 1.
Figure 6:
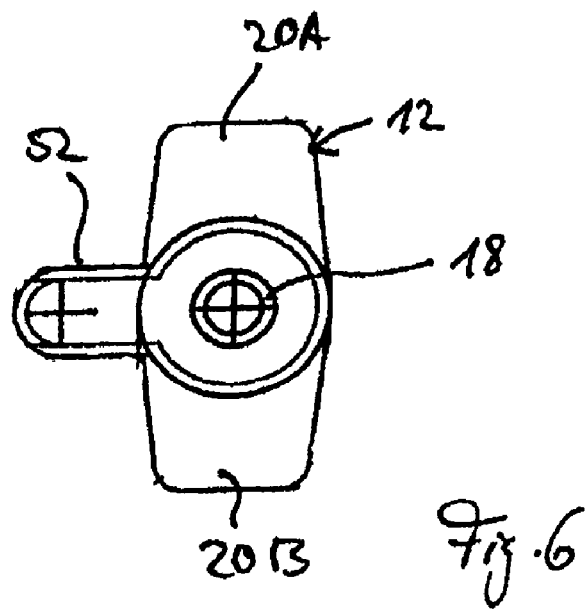
FIG. 6 is a frontal view of the retaining body.

In a second step, piston 22 is retracted into the position shown in FIG. 2, so that a cotton swab or the like to which a saliva specimen has been applied can be inserted via the insertion channel 52 into the liquid contained in the retaining space 46. Then the cotton swab is removed from the retaining body 12 through the insertion channel 52. Then in a third step piston 22 is moved back into the position shown in FIG. 1.

In the next and fourth step, application unit 16 is displaced in the direction of the retaining body 12, so that the locking pin 36 is in an activation position and a flow path is established between the retaining space 46 and nozzle 32 via transverse channel 44 and axial channel 42. By applying pressure to the pressure plate 28 of the piston unit 14, it is then possible to dispense the test liquid to which the saliva specimen has been added out of the retaining body 12 via the nozzle 32.

Figure 7:
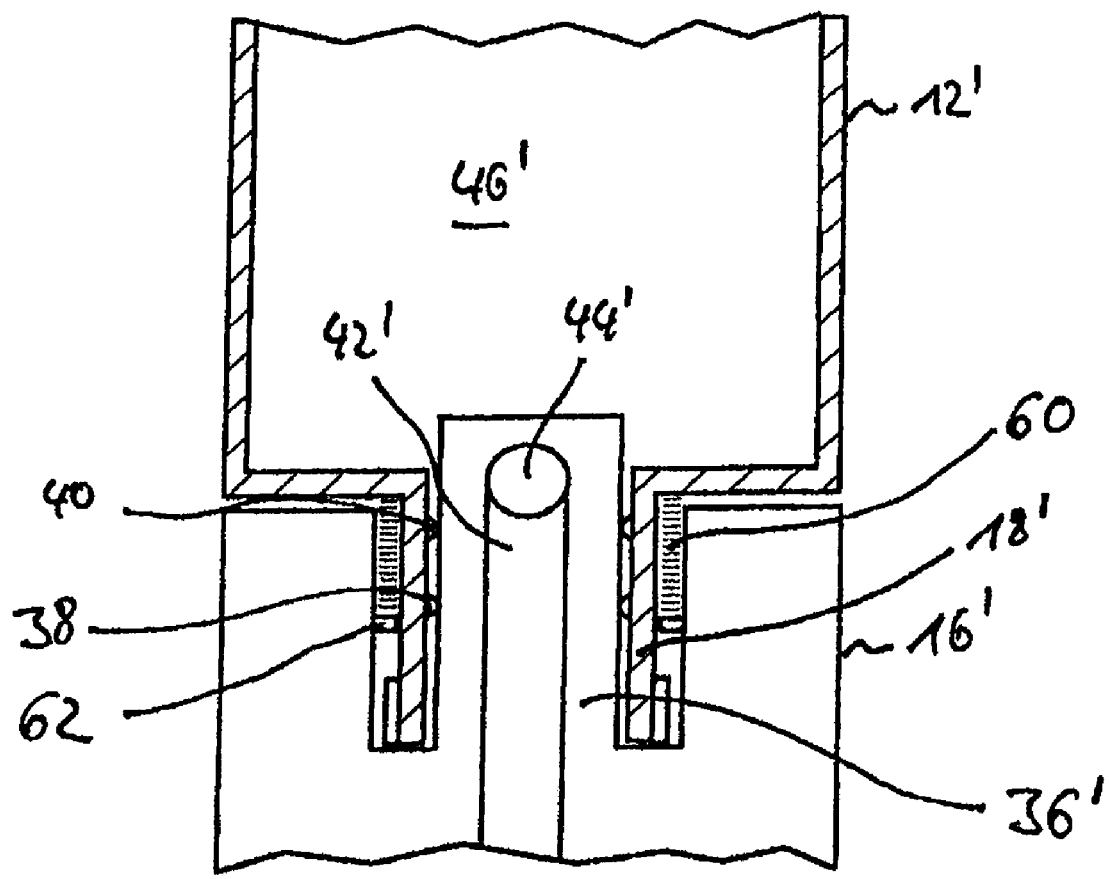
FIG. 7 is a section view through a device incorporating the invention and having an automatic closing device in the area of a dispensing nozzle.

In a proximal end position in which the retaining space 46 is essentially emptied, the front face of piston 22 is then in contact with the free frontal face of the locking pin 36 of application unit 16. FIG. 7 shows the proximal area of a retaining body 12' of the type depicted in FIGS. 1 through 6 to which an application device 16' is attached, which could be a pipette tip, a cannula or the like.

The application unit 16' is provided with a locking pin 36' of the type shown in greater detail in FIGS. 1 through 4, which engages in a dispensing nozzle 18' of the retaining body 12' and comprises a transverse channel 44' and an axial channel 42', whereby the transverse channel 44' interacts with sealing lips 38 and 40 which are formed on the inside of the dispensing nozzle 18' of the retaining body 12' to which the application unit 16' is attached.

In the closed position of the locking pin 36', the application unit 16' and thus also the locking pin 36' are biased by a helical spring 60 surrounding the dispensing nozzle 18' so that locking pin 36' automatically snaps backs into the closed position from the activation position as depicted in FIG. 7 when released accordingly.

Helical spring 60 is therefore stretched between a frontal face of the retaining body 12' that forms a support and a ring collar 62 of the application unit 16'.

To prevent the application unit 16' from becoming inadvertently detached from the retaining body 12', catch means formed by a ring collar 62 of the dispensing nozzle 18' are preferably arranged between the application unit 16' and the dispensing nozzle 18'. These catch means may also be designed as fixation means for securing the closed position and the activation position of locking pin 36'.

FIGS. 8 through 14 show another embodiment of an inventive design of the device 70 for storing and dispensing a free-flowing substance. The device 10 again essentially is composed of three units, namely an essentially cylindrical retaining body 12", a piston unit 14" and an adapter device 16".

The retaining body 12" comprises an essentially cylindrical base body which is provided on one front face with a dispensing nozzle 18" which is also designed to be cylindrical. On its end facing away from the dispensing nozzle 18", the retaining body 12" has an elliptical collar 20" against which a user's ring finger and middle finger, for example, can rest when activating the piston unit 14". The piston unit 14" is designed according to the piston unit of the embodiment according to FIGS. 1 through 6.

The adapter device 16" is formed from a tubular piece whose end facing the retaining body 12" forms a locking pin 36" and whose end facing away from the retaining body 12" is designed for connecting to an applicator such as a cannula or a tube.

The locking pin 36" is inserted into the dispensing nozzle 18" of the retaining body 12" and interacts with two sealing lips 38 and 40 that are formed in one piece on the inside of the dispensing nozzle 18 and are separated from one another in the axial direction of the retaining body 12".

The locking pin 36" has an axial channel 42 which opens on the side of the sealing plate 34 facing the front lateral plate 30 and is connected to a transverse channel 44 which passes through the locking pin 36". The transverse channel 44 has a diameter slightly smaller than the axial distance between the two sealing lips 38 and 40, so that the locking pin 36" is set in a closed position when the transverse channel 44 is arranged between the two sealing lips 38 and 40, and set in an activation position when the transverse channel 44 is displaced beyond the sealing lips 40 into a retaining space 46 of the retaining body 12" so that a liquid contained in the retaining space 46 can be dispensed through the transverse channel 44 and the axial channel 42 by depressing the piston unit 14".

Figure 8:
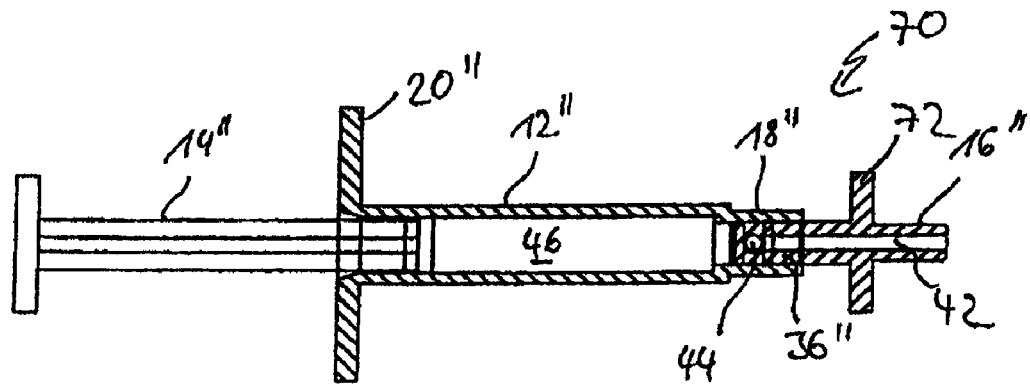
FIG. 8 is a longitudinal section view through another embodiment in the closed position.
Figure 9:
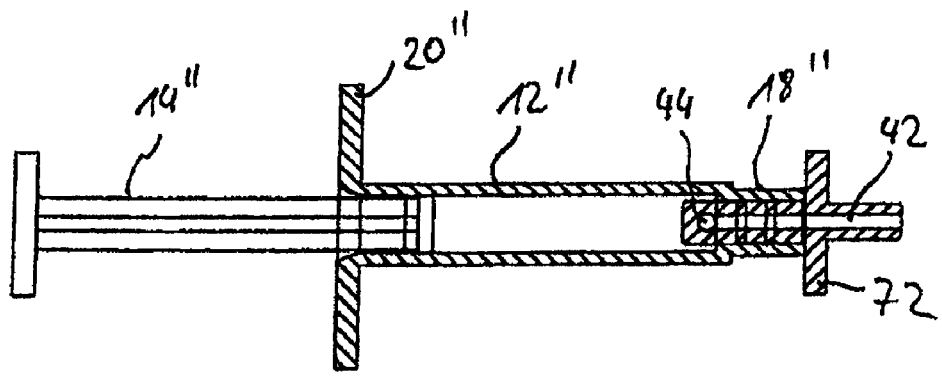
FIG. 9 is a longitudinal section view through the device according to FIG. 8 in the activated condition.
Figure 10:
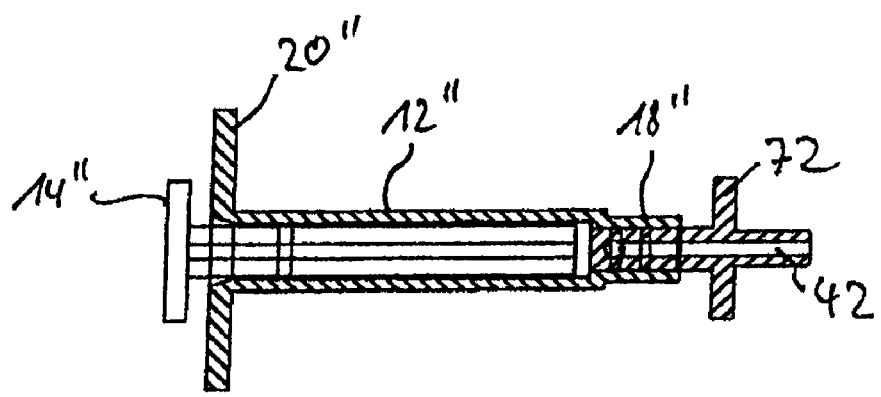
FIG. 10 is a longitudinal section view through the device according to FIG. 9 in the emptied condition.
Figure 11:
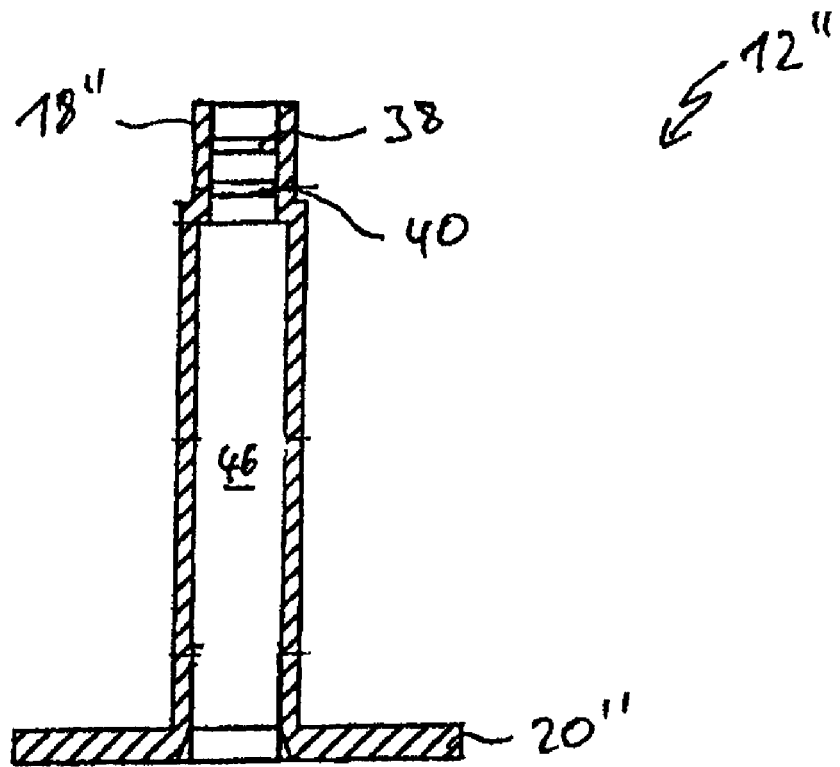
FIG. 11 is a longitudinal section view through a retaining body of the device according to FIG. 8, shown alone.
Figure 12:
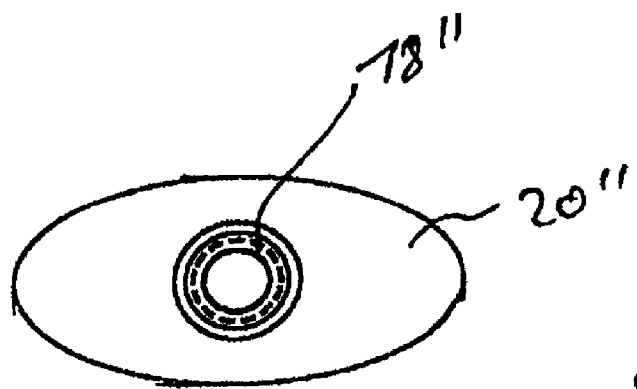
FIG. 12 is a front view of the retaining body.
Figure 13:
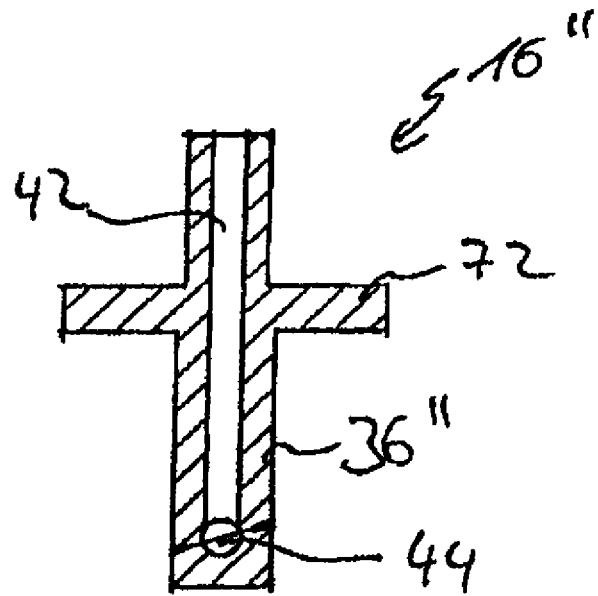
FIG. 13 is a longitudinal section view through an adapter device of the device according to FIG. 8.
Figure 14:
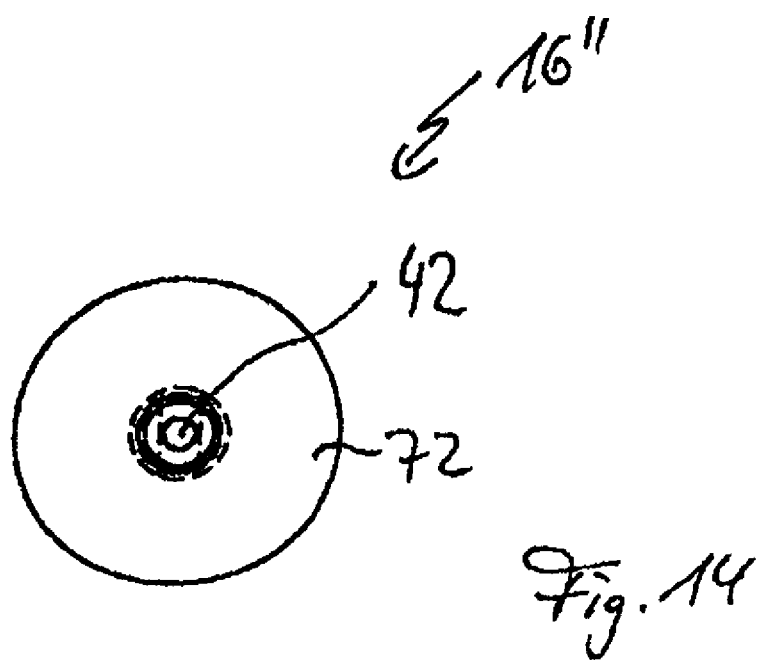
FIG. 14 is a front view of the adapter device.

FIG. 8 shows the device 70 in the deactivated state. FIG. 9 shows the device 70 in the activated state in which the adapter device 16" has been displaced in the direction of the retaining body 12" to such an extent that the ring collar 72, which serves as an activation aid is in contact with the free front face of the dispensing nozzle 18" and a connection is established between the retaining space of the retaining body 12" and the axial channel 42 of the adapter device leading to the environment. FIG. 10 shows the device 70 in the emptied state in which the piston unit 14" is in contact with the locking pin 36".

FIGS. 15 through 19 show a third embodiment of a device 80 for storing and dispensing a free-flowing substance. Pursuant to the embodiments described above, the device 80 is comprised essentially of three units, namely an essentially cylindrical retaining body 12''', a piston unit 14''' and an application unit 16'''.

The piston unit 14''' corresponds to that according to FIGS. 8 through 10. The cylindrical retaining body 12''' differs from that according to FIGS. 11 and 12 in that an outlet opening 82 which develops into an outlet nozzle 18''' is connected to the retaining space 46. On the inside of the outlet nozzle 18''', a locking pin 36''' of the application unit 16''' is provided, with a transverse channel 44 passing through it according to the embodiments described above, and with an axial channel 42 being connected thereto and leading to the environment. The locking pin 36''' comprises a guide section 87 having an enlarged diameter and a sealing section 89 having a reduced diameter, these two being separated from one another by a sealing face 91.

Figure 15:
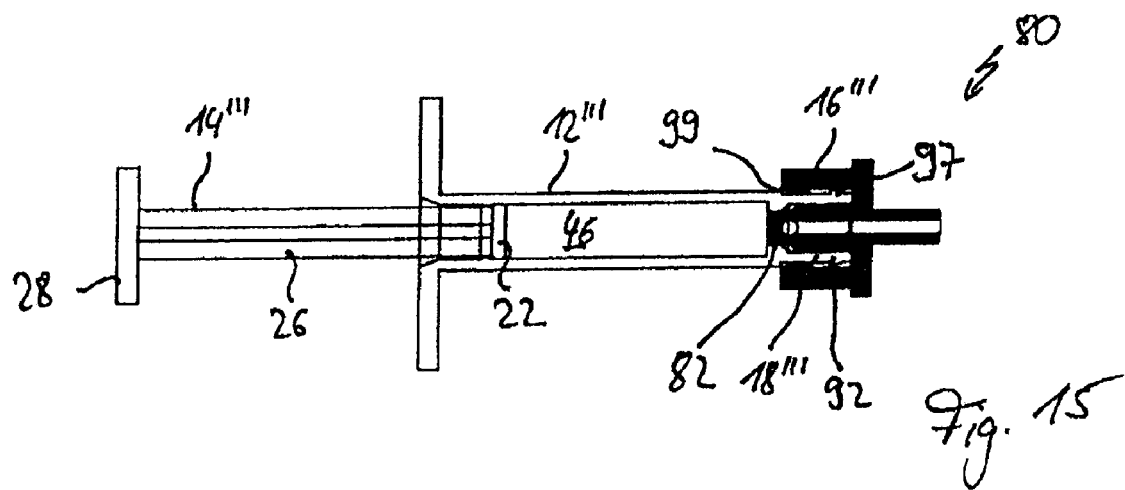
FIG. 15 is a longitudinal section view through a third embodiment of a syringe-like device incorporating the invention in the closed position.
Figure 16:
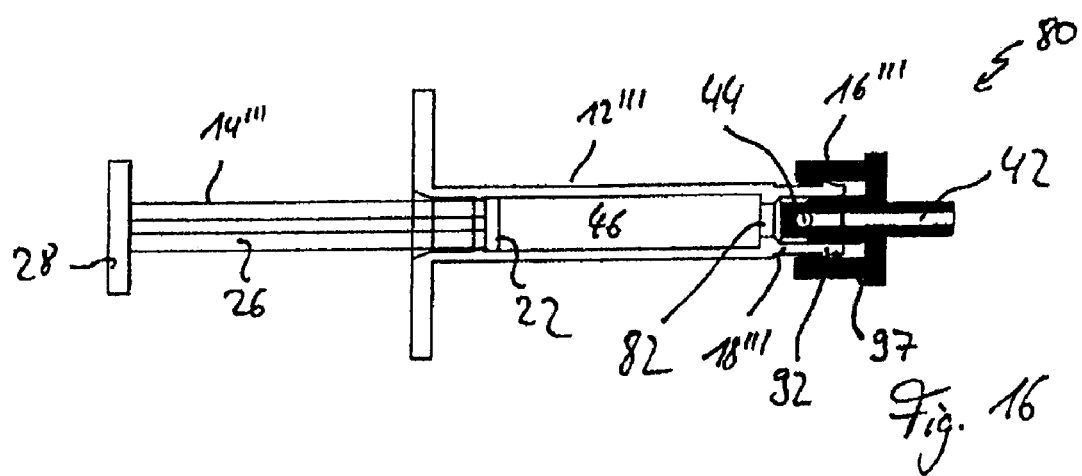
FIG. 16 shows the syringe-like device according to FIG. 15 in the activation position.
Figure 17:
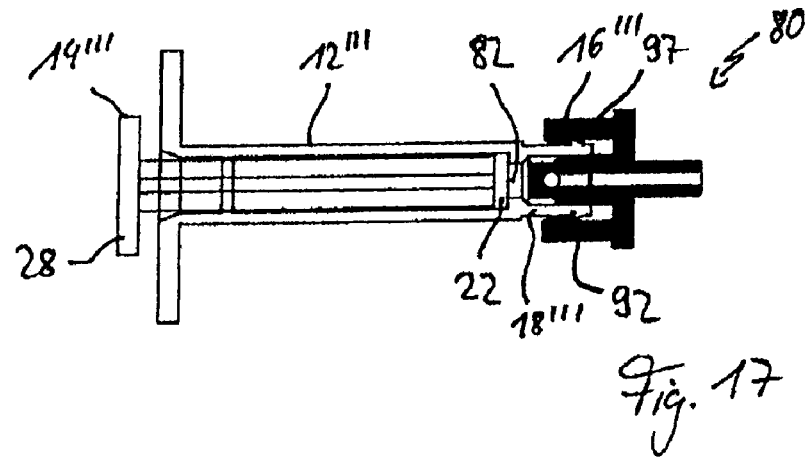
FIG. 17 shows the syringe-like device according to FIG. 15 in the emptied condition.
Figure 18:
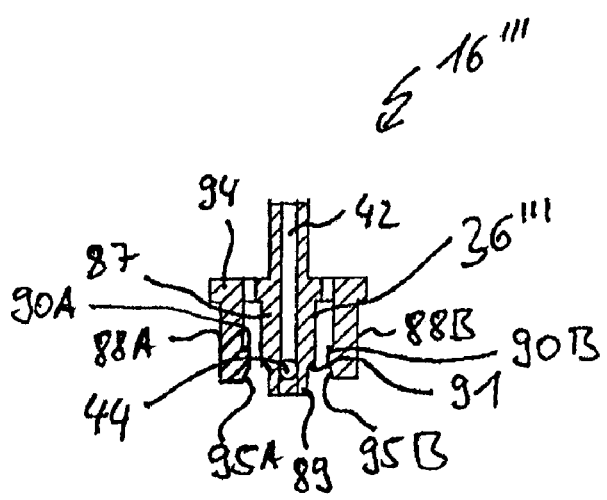
FIG. 18 is a longitudinal section view through an application device of the syringe-like device according to FIGS. 15 through 17 and FIG. 19 is a side view of the application device according to FIG. 18.
Figure 19:
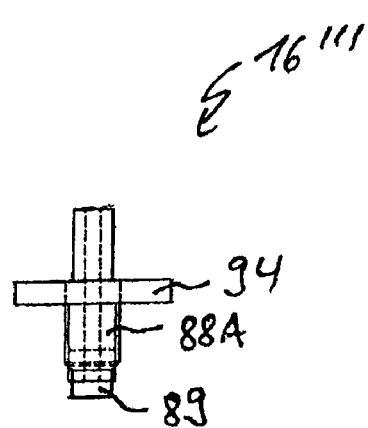

In the closed position depicted in FIG. 15, the sealing section 89 engages in the outlet opening 82 of the retaining space 46, and the conical sealing face 91 is in sealing contact with a corresponding face 93 on the inside of the dispensing nozzle 18'''. The application unit 16''', which is depicted alone in each of FIGS. 18 and 19, also has a base plate 94 with two legs 88A and 88B protruding away from it in the direction of the retaining body 12''' and parallel to the axis of the axial channel 42, serving to secure the application unit 16''' to the dispensing nozzle 18'''. The legs 88A, 88B are each designed to be elastic or are mounted on the base plate 94 and provided with a catch nose 90A and 90B, respectively, cooperating with a catch collar 92 on the circumference of the dispensing nozzle 18''' and thereby securing the application unit 16''' on the dispensing nozzle 18'''.

To be able to easily attach the application unit 16''' to the dispensing nozzle 18''' and/or easily insert the locking pin 36''' into the dispensing nozzle 18''', the catch collar 92 has a beveled edge 97 on its side facing away from the retaining space 46, said beveled edge cooperating with beveled edges 95A and 95B on the legs 88A and 88B when the application unit 16''' is pushed into place.

In the closed position shown in FIG. 15, the sealing section 89 of the locking pin 36''' engages in the outlet opening 82 of the retaining space 46. The free front faces of the legs 88A, 88B here are in contact with a ring collar 99 forming a stop on the retaining body 12'''. To activate the device 80, the application unit 16''' is displaced in the direction away from the piston unit 14''' with respect to the retaining body 12''' until the catch noses 90A, 90B of the legs 88A, 88B are stopped against the catch collar 92 of the dispensing nozzle 18'''. The sealing section 89 of the locking pin 36''' is thereby pulled out of the outlet opening 82. A fluid connection is thereby established through the outlet opening 82 between the retaining room 46 of the retaining body 12''' and the transverse channel 44 of the application unit 16'''. By means of manual axial pressure applied to the piston unit 14''' in the direction of the application unit 16''', the free-flowing substance contained in the retaining space 46 can then be dispensed from the device 80 and applied.

I claim:

1. A device for retaining and dispensing a free-flowing substance, comprising
    a syringe-like retaining body defining a retaining space for retaining a free-flowing substance;
    a displaceable piston axially introduced into said retaining space;
    a dispensing nozzle provided on a front end of the retaining body facing away from the piston, the dispensing nozzle includes two inwardly extending ring-shaped sealing lips;
    a locking pin engaging the two ring-shaped sealing lips of the dispensing nozzle;
    at least one transverse channel passing through the locking pin and the at least one transverse channel has a diameter which is equal to or less than a distance between the two sealing lips; and
    an axial channel branching off from the at least one transverse channel, whereby in a closed position of the locking pin, a flow connection between the transverse channel and the retaining space is blocked by one of said sealing lips, and in an activation position of the locking pin, a flow connection between the transverse channel and the retaining space is open, so that the free-flowing substance can be dispensed from the retaining space via the transverse channel and the axial channel.

2. The device according to claim 1, in which the retaining body has an insertion channel for a substance.

3. The device according to claim 2, in which the insertion channel has a single-sided funnel-shaped widening of a wall of the retaining body in an end area facing away from the dispensing nozzle.

4. The device according to claim 1, in which the locking pin is part of an application device and/or an adapter device.

5. The device according to claim 4, in which the application device is a cannula.

6. The device according to claim 4, in which the application device is provided with a nozzle.

7. The device according to claim 1, in which the locking pin is supported by a spring and is prestressed in the closed position.

8. The device according to claim 7, in which the spring is encapsulated.

9. The device according to claim 7, in which the spring surrounds the dispensing nozzle.

10. The device according to claim 1, in which the locking pin can be secured by a fixation devices in the closed position and/or in the activation position.

11. A device for retaining and dispensing a free-flowing substance, comprising
    a retaining body defining a retaining space for retaining a free-flowing substance;
    a piston slidably received in said retaining space;
    a dispensing nozzle in fluid communication with said retaining space;
    a locking pin in fluid communication with said retaining space and mounted in said dispensing nozzle, said locking pin having at least one transverse channel passing through the locking pin and an axial channel branching off from the at least one transverse channel, whereby in a closed position of the locking pin, a flow connection between the transverse channel and the retaining space is blocked by a radially inwardly extending ring-shaped sealing lip located between said transverse channel and said retaining space, said sealing lip extending from said dispensing nozzle and engaging said locking pin, and in an activation position of the locking pin, in which said transverse channel of said locking pin is positioned between said ring shaped sealing lip and said retaining space, a flow connection between the transverse channel and the retaining space is open, so that the free-flowing substance can be dispensed from the retaining space via the transverse channel and the axial channel.

12. The device according to claim 11, including a second ring shaped sealing lip extending from the dispensing nozzle and engaging said locking pin between said transverse channel and a distal end of said dispensing nozzle, said transverse channel having a diameter which is equal to or less than a distance between the two sealing lips.

* * * * *